United States Patent
Despres

(10) Patent No.: US 9,451,770 B2
(45) Date of Patent: Sep. 27, 2016

(54) METHOD OF ACTIVATING IMMUNE RESPONSE IN PLANTS

(71) Applicant: Charles Despres, St. Catharines (CA)

(72) Inventor: Charles Despres, St. Catharines (CA)

(*) Notice: Subject to any disclaimer, the term of this patent is extended or adjusted under 35 U.S.C. 154(b) by 210 days.

(21) Appl. No.: 13/912,875

(22) Filed: Jun. 7, 2013

(65) Prior Publication Data

US 2014/0031234 A1   Jan. 30, 2014

Related U.S. Application Data

(60) Provisional application No. 61/657,461, filed on Jun. 8, 2012.

(51) Int. Cl.
| | | |
|---|---|---|
| *A01N 37/40* | (2006.01) | |
| *G01N 33/566* | (2006.01) | |
| *A01N 61/00* | (2006.01) | |
| *G01N 33/569* | (2006.01) | |

(52) U.S. Cl.
CPC ............... *A01N 37/40* (2013.01); *A01N 61/00* (2013.01); *G01N 33/566* (2013.01); *G01N 33/56961* (2013.01)

(58) Field of Classification Search
None
See application file for complete search history.

(56) References Cited

PUBLICATIONS

Tada et al. Plant immunity requires conformational charges of NPR1 via S-Nitrosylation and Thioredoxins, Science 321: 952-956, 2008.*

* cited by examiner

*Primary Examiner* — Michele K Joike
(74) *Attorney, Agent, or Firm* — Gowling WLG (Canada) LLP

(57) ABSTRACT

A method of enhancing plant immunity is provided. The method comprises the step of administering to a plant a small molecule that binds to NPR1, or a functionally equivalent homolog thereof, that disrupts the interaction between N-terminal BTB/POZ domain and the C-terminal transactivation domain of NPR1. A method of screening for small molecule compounds that enhance plant immunity is also provided.

9 Claims, 9 Drawing Sheets

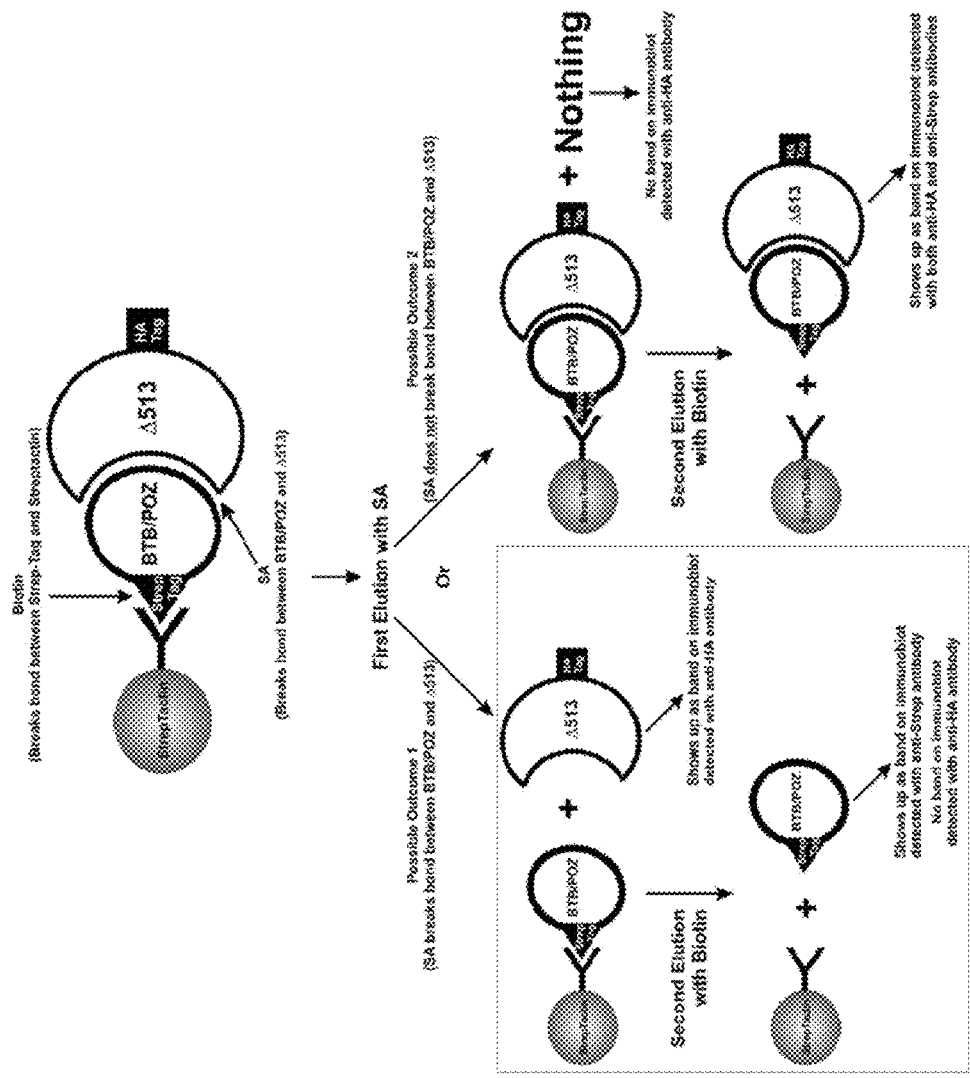

Figure 9

AtNPR1
AVLDQIMNCEDLTQLACGEDDTAEKRLQKKQRYMEIQETLKKAFSEDNLELGNSS
LTDSTSSTSKSTGGKRSNRKLSHRRR

TcNPR1
EVLNKIMDADDLSQLACGGNDTPEERLVKKQRYVELQDVLSKAFNEDKVEFDRST
ISSSSSSKSIGVSRPNGKLTGSGRGG

GhNPR1
EVLNKIMDADDLSQLACGGIDTAEERVVKRQRYMELQDVLSKAFHEDKEQFDRSA
ISSSSSSKSIVVTGPKGKAHCYS

NtNPR1
EVLNKIMDADDLSEIAYMGNDTAEERQLKKQRYMELQEILTKAFTEDKEEFDKTN
NISSSCSSTSKGVDKPNKLPFRK

OsNPR1
NVLDKIMDDETDPVSLGRDTSAEKRKRFHDLQDVLQKAFHEDKEENDRSGLSSSS
SSTSIGAIRPRR

METHOD OF ACTIVATING IMMUNE RESPONSE IN PLANTS

CROSS REFERENCE TO RELATED APPLICATIONS

This application claims the benefit of U.S. Provisional Patent Application No. 61/657,461, filed Jun. 8, 2012, the disclosure of which is incorporated fully herein by reference.

FIELD OF THE INVENTION

The present invention relates to Systemic Acquired Resistance (SAR) in plants, and more particularly, to methods of activating plant immune response.

BACKGROUND OF THE INVENTION

Salicylic acid (SA) serves as an endogenous phytohormone in the deployment of Systemic Acquired Resistance (SAR), a broad-spectrum and long-lasting immune response activated by avirulent pathogens in plants. Its deployment is monitored through the marker gene PR-1, whose activation requires the recruitment of an SA-dependent transcriptional enhanceosome to its promoter. The enhanceosome contains members of the TGA2 Glade of bZIP transcription factors and the transcriptional coactivator NPR1, which is the central regulator of SAR and SA-dependent gene activation. TGA2 is a transcriptional repressor and thus requires a coactivator to effect gene activation. NPR1 provides a dual function in the enhanceosome. First, its N-terminal region contains a BTB/POZ domain which interacts with and negates the function of the TGA2 repression domain, and secondly, NPR1 harbors in its C-terminal region a transactivation domain, which contains two cysteines ($Cys^{521}$ and $Cys^{529}$) required for the activating function of the enhanceosome.

In non-SA-stimulated cells, NPR1-GFP fusion proteins behave as oligomers on sodium dodecyl-sulfate-polyacrylamide gel (SDS-PAGE) electrophoresis. Endogenous NPR1 localizes to both the nucleus and the cytosol and nuclear localization is critical to PR-1 activation. A fraction of the nuclear NPR1 population acts as a latent coactivator which is recruited under non-inducing conditions to the PR-1 promoter. There thus exists an uncharacterized mechanism by which the NPR1 transactivating domain remains occluded under non-inducing conditions and gets unveiled during SA-dependent gene activation. Furthermore, although genetic analyses have revealed many genes involved in SA-signaling, the receptor responsible for sensing SA and leading to direct or indirect NPR1 activation remains elusive.

While enzymes, such as catalase, peroxidase, and methylsalicylate esterase, have been shown to directly interact with SA, their proposed role in SAR has not been unequivocal. SA was originally portrayed as a catalase and peroxidase inhibitor, leading to the generation of $H_2O_2$, and the production of PR protein. However, $H_2O_2$ was later shown not to be a second messenger acting downstream of SA, invalidating the role of catalase and peroxidase as SA-receptors for PR gene activation. Whereas methyl-salicylate esterase has been shown to play a role in tobacco, it clearly has no role in SAR in *Arabidopsis*. Most importantly, these enzymes do not figure as classical transcription regulators and therefore, they are unlikely to regulate gene expression directly.

It would be desirable to develop novel methods of activating the immune response in plants in order to enhance immunity in plants.

SUMMARY OF THE INVENTION

It has now been determined that NPR1 is the receptor for salicylic acid, and specifically interacts with salicylic acid. This determination permits the targeted enhancement of plant immunity, as well as the identification of potential plant immunity-enhancing compounds.

Thus, in one aspect of the present invention, a method of enhancing plant immunity is provided comprising the step of administering to a plant a small molecule that binds to NPR1, or a functionally equivalent salicylic acid-binding protein, and disrupts the interaction between N-terminal BTB/POZ domain and the C-terminal transactivation domain of the NPR1 protein.

In another aspect, a method of identifying small molecule compounds that enhance plant immunity is provided. The method comprises the step of screening a candidate compound for binding to the NPR1 C-terminal transactivation domain and determining whether or not the compound binds to the NPR1 protein, wherein a compound that exhibits a binding affinity for the NPR1 C-terminal transactivation domain is a candidate compound that may enhance plant immunity.

These and other aspects of the invention are described in the detailed description by reference to the following figures.

BRIEF DESCRIPTION OF THE FIGURES

FIG. 8. Schematics and outcomes of the BTB/POZ-Δ513 pull-down assays. The boxed diagram indicates the outcome observed in FIG. 5C.

FIG. 9. Amino acid sequences of the C-terminus of NPR1 protein from different plants.

DETAILED DESCRIPTION OF THE INVENTION

Figure 1:
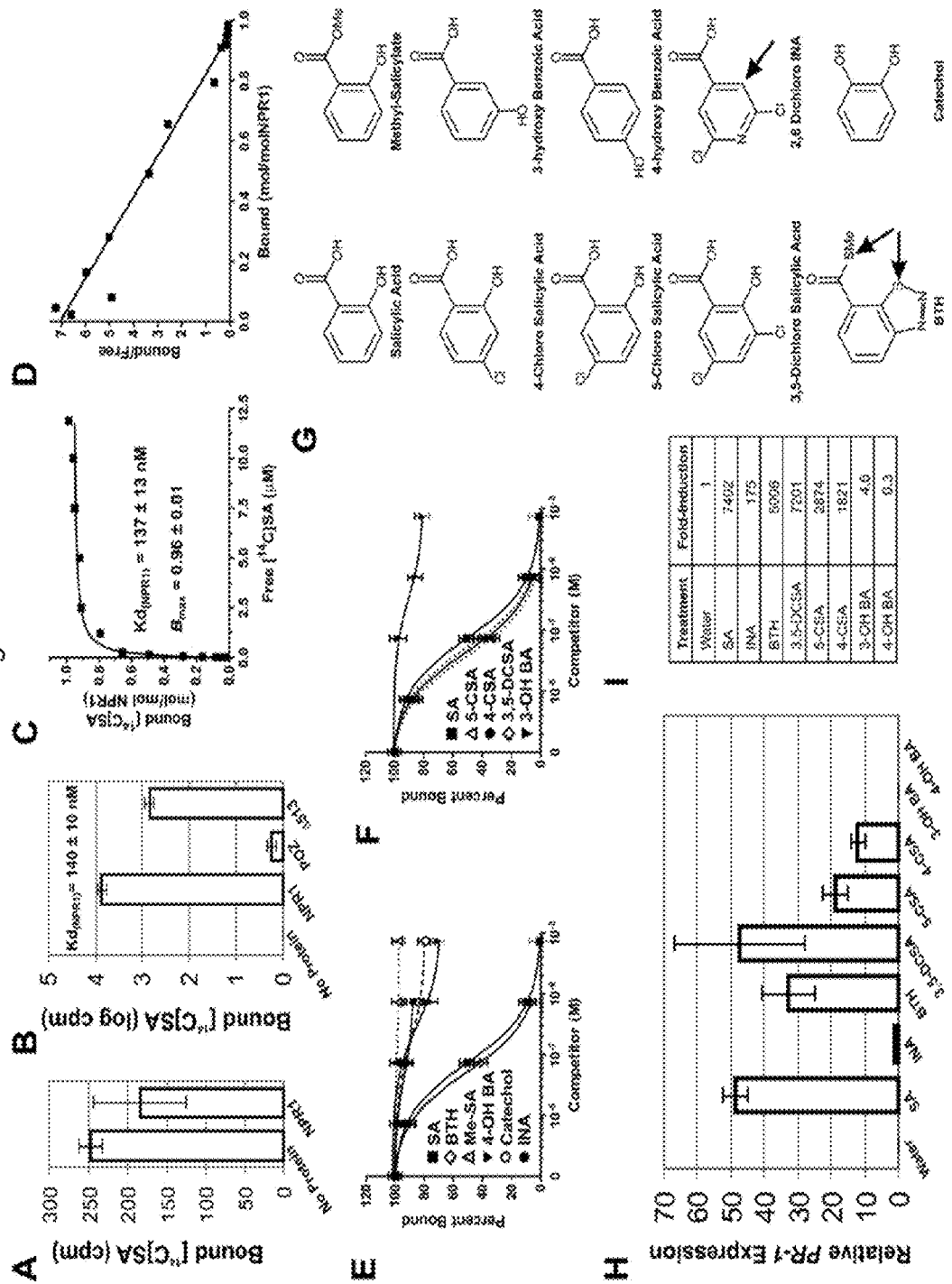
FIG. 1. [$^{14}C$]SA binding of no protein, NPR1, the BTB/POZ of NPR1 (POZ), or the transactivation domain of NPR1 (Δ513) using (A) a classical non-equilibrium solid-phase method or (B) equilibrium dialysis; (C) saturation binding of [$^{14}C$]SA to NPR1 using equilibrium dialysis; (D) Scatchard Plot of the data in (C); (E) Homologous and (F) heterologous competitive binding curves for the [$^{14}C$]SA-NPR1 interaction using equilibrium dialysis; (G) illustrates structures of the competitors; (H) Quantitative RT-PCR; and (I) Fold-induction of a given chemical treatment over a water control, calculated using data from (H).

The present invention relates to a method of enhancing plant immunity by PR-1 gene activation. The method comprises the step of administering to a plant a small molecule that binds to NPR1, or binds to a functionally equivalent salicylic acid receptor protein (NPR), and disturbs the interaction between N-terminal BTB/POZ domain and the C-terminal transactivation domain of NPR1.

The term "NPR1" or "NIM1" refers to a plant transcriptional coactivator that is involved in PR (pathogenesis-related) gene activation. The term "NPR1" as used herein is meant to encompass NPR1 proteins in plants including, but not limited to, Arabidopsis, Theobroma, tobacco, cotton, rice, legume and the like. Amino acid sequences of the C-terminal transactivation domain of NPR1 are set out in FIG. 9, and include the sequence of the C-terminus of the NPR1 protein from Arabidopsis thaliana (AtNPR1)(SEQ ID NO: 13), as well as the sequence of the C-terminus of NPR1 receptor proteins in Theobroma cacao (TcNPR1)( SEQ ID NO: 14), Gossypium hirstum (GhNPR1)(cotton)( SEQ ID NO: 15), Nicotiana tabacum (NtNPR1)(tobacco)( SEQ ID NO: 16), and Oryza sativa (OsNPR1)(rice)( SEQ ID NO: 17), as well as functionally equivalent NPR receptors. The term "functionally equivalent" as it is used herein is meant to refer to other NPR salicylic acid receptor proteins in plants, such as NPR5 and NPR6.

The present method includes the step of PR gene activation by administration of a small molecule that binds to a salicyclic acid receptor protein, such as NPR1, and disturbs the interaction between N-terminal BTB/POZ domain and the C-terminal transactivation domain of NPR1, or a functionally equivalent salicylic acid receptor protein. The term "small molecule" refers to a molecule having a molecular weight of less than 5 kilodaltons (kD), preferably less than 2.5 kD, and more preferably, a molecule having a molecular weight of 1 kD or less, and are herein referred to as "NPR-binding".

An NPR-binding small molecule in accordance with the present invention may have the following general formula:

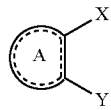

wherein X and Y are each an electronegative functional group that together can coordinate a transition metal such as copper; and ring A is a hydrophobic cyclic core. Examples of electronegative functional groups include groups containing, for example, oxygen, nitrogen and sulfur, such as hydroxyl, carbonyl, amine, —NHR wherein R is a lower alkyl group, nitro, —SH, —COH, —OCOH and —CH$_2$OH.

Ring A may, for example, be selected from the group consisting of phenyl, heterocyclyl, cyclohexyl and cyclopentyl, and may optionally be substituted with one or more groups selected from, for example, halogen, e.g. chlorine, fluorine, bromine; hydroxyl, thio, $C_1$-$C_6$ alkyl, $C_1$-$C_6$ alkyl halide, —OR$^1$, —NH$_2$, —NO$_2$, —NHR$^1$, —NR$^1$R$^2$ or —SR$^1$, fused phenyl and fused heterocyclyl. The variables R$^1$ and R$^2$ are independently selected from the group consisting of $C_1$-$C_6$ alkyl, $C_1$-$C_6$ alkyl halide, $C_1$-$C_6$ alkanol and $C_1$-$C_6$ alkoxy.

The term "heterocyclyl" is used herein to encompass ring structures that include at least one hetero atom selected from O, S and N within the core ring structure, and preferably 5- and 6-membered ring structures such as, but not limited to, furan, thiophene, pyrrole, pyran, pyrimidine, piperazine, thiazine and oxazine. Examples of fused heterocyclyl-containing rings, or bicyclic hydrophobic cores include, but are not limited to, benzothiophene, quinoline, isoquinoline, indole, benzofuran and purine. An example of a fused non-heterocyclyl-containing ring structure is naphthalene.

The NPR-binding small molecule is administered to the plant in an concentration ranging from about 10-1000 micromolar, and more preferably, a concentration from about 100 to 500 micromolar.

As one of skill in the art will appreciate, NPR-binding small molecule may be administered to a plant in a suitable agriculturally acceptable formulation, including but not limited to, a growing medium such as soil or hydroponic liquid medium, dusts, granules, solution concentrates, emulsifiable concentrates and wettable powders. The term "agriculturally acceptable" indicates that the formulation is non-toxic and otherwise acceptable for application to a plant, whether applied indoors (e.g. in a contained environment) or outdoors (e.g. in a non-contained environment that is exposed to other plant, animal and human life). The formulation may include additives such as solvents, for example ketones, alcohols, aliphatic ethers; surfactants, for example aliphatic alcohol sulfates, alkylphenol ethoxylates, Silwet; or other additives such as fillers and carriers, for example clay and minerals; and plant extracts, such as nut shells and guar gum.

The NPR-binding molecule may be administered to a plant in a composition including one or more additional plant growth-enhancing compounds, including but not limited to, macronutrients such as a nitrogen source (e.g. ammonium, nitrates and the like), a phosphorous source (e.g. phosphoric acid), and a potassium source (e.g. potash), micronutrients such as boron, iron, calcium, magnesium, sulfur, selenium, manganese, molybdenum, zinc and iodine, and vitamins and cofactors such as thiamine, riboflavin, niacin (nicotinic acid and/or niacinamide), pyridoxine, panthenol, cyanocobalamin, citric acid, folic acid, biotin and combinations thereof.

While a clear advantage of the present method of enhancing plant immunity is to minimize or avoid the use of toxic pesticides and herbicides, an NPR-binding molecule may be administered to a plant in combination with insecticides such as organophosphates, pyrethroids and neonicotinoids, inorganic materials such as aresenates, copper and sulfur, and biological control agents such as *Bacillus* spp.

An additional step in the method may include administration of a transition metal, e.g. copper, to the plant with or following administration of the selected small molecule. Soil generally contains sufficient copper to coordinate with an NPR-binding small molecule administered to a plant; however, in the event that the soil is transition metal-free, or substantially transition metal-free (e.g. less than about 9 ppm transition metal content in the soil), or in the event that plant growing media other than soil is being used (for example, water or other liquid growing medium) that is transition metal-free, transition metal may be administered to plant in an amount of at least about 9 ppm, and preferably an amount in the range of 9 to 30 ppm if applied to the soil or other growing medium of the plant, or in amount of about 50 to 300 micromolar if applied directly to a plant in a formulation that may also include the NPR-binding molecule, or in a formulation separate from the NPR-binding molecule. In this regard, transition metal, for example copper, is generally administered to the plant or admixed with the formulation in the form of a salt, for example, sulfate, chloride, bromide, fluoride, iodide, d-gluconate, hydroxide, molybdate, nitrate, perchlorate or thiocyanate. Alternatively, the metal may be administered as a chelate, for example as an ethylenediamine (EDTA), ethanolamine, triethanolamine or salicylate chelate.

In another aspect, a method of identifying small molecule compounds that enhance plant immunity is provided. The method comprises the step of screening a small molecule candidate compound for NPR binding, and specifically, binding to the C-terminal transactivation domain of NPR1 or of a functionally equivalent salicylic acid receptor protein. The function of the small molecule to bind this C-terminal region of NPR1 may be determined using established binding assays as described herein. For example, NPR binding may be determined using an assay in which the NPR is immobilized on a solid phase followed by treatment with a detectably labeled molecule, e.g. a radioactive, colorimetric or enzymatic label. Other methods to determine NPR1 binding may also be used, as one of skill in the art will appreciate, for example, equilibrium dialysis or isothermal titration calorimetry. Small molecules determined to exhibit a binding affinity to the C-terminal transactivation domain of an NPR that is similar to that of salicylic acid for NPR1, e.g. a $k_d$ of about 50 μM or less, for example, 40 μM or less, 30 μM or less, 20 μM or less, or 10 μM or less, are candidate compounds that may enhance plant immunity.

NPR-binding small molecule candidate compounds may be further screened to determine whether or not NPR-binding is metal dependent, e.g. whether or not the candidate compound has the ability to coordinate transition metals, and in particular, copper. In this regard, binding assays to determine if the candidate compound binds to a mutated C-terminal NPR activation region, e.g. including $Cys^{521/529}$ mutations (e.g. mutation of the cysteine or replacement of cysteine with another amino acid to eliminate metal binding), or binds to the C-terminal region of the NPR in the presence of EDTA, may be used. Candidate compounds which do not bind to a mutated C-terminal NPR activation region, or to the C-terminal region of NPR in the presence of EDTA, exhibit metal dependent NPR binding and such compounds are candidate compounds that may be useful to activate PR-1 genes and enhance plant immunity.

Embodiments of the invention are described by reference to the following specific example which is not to be construed as limiting.

EXAMPLE

Experimental Procedures
Protein Purification for Equilibrium Dialysis, ICP-MS and Scintillation Proximity Assay Proteins were expressed in *E. coli* as N-terminal fusions to the Strep-Tag according to standard protocols. Recombinant proteins were purified using 1 ml Strep-Tactin Superflow Plus columns (Qiagen) according to the manufacturer's protocol. The Strep-Tactin buffer contained 50 mM sodium phosphate at pH 8.0 and 300 mM NaCl. For ICP-MS analyses, the buffer did not contain NaCl and used metal-free water. For equilibrium dialysis that contained EDTA, bound proteins were treated with 10 ml of 50 mM EDTA followed by 10 ml of 5 nM EDTA, prior to elution with a buffer containing 5 nM EDTA. Protein concentrations were measured by Bradford assays according to the manufacturer's instruction (Bio-Rad) using BSA as a standard. For metal determination from proteins expressed in *Arabidopsis*, extracts from SA-treated plants were immunoprecipitated with an anti-NPR1 antibody as described previously (Rochon et al. 2006. Plant Cell 18, 3670-3685). Protein concentrations were based on sulfur content determined by ICP-MS. NPR1 was cloned in pGEX-4T-1 as a BamH1/Not1 fragment and expressed as described above. NPR1-GST was purified using 1 ml GSTrap FF column (GE Health) and cleaved on-column using thrombin as described by the manufacturer (GE Health). The eluted NPR1 was purified by 5300 gel chromatography and recovered from the void fraction.

Metal-Affinity Chromatography

Proteins were expressed in *E. coli* as N-terminal fusions to the HA-Tag according to standard protocols. Crude lysates were loaded on 1 ml HisTrap FF columns (GE Health) according to the manufacturer's protocol. The HisTrap buffer contained 50 mM HEPES at pH 7.5, 40 mM imidazole, and 150 mM NaCl. Where indicated, the HisTrap matrix was stripped of metal using 10 column-volume of 50 mM EDTA followed by 10 column-volume of 5 nM EDTA. Elution was performed in the HisTrap buffer supplemented with 1 M imidazole.

Pull-Down Assays

The BTB/POZ (amino acids 1-190 of NPR1) was expressed in *E. coli* as a C-terminal fusion to the Strep-Tag according to standard protocols. The Δ513 of NPR1 was expressed as an N-terminal fusion to the HA-Tag as described above. The VLRSgt (as described in Hall et al. (2007) Plant J 49, 579-591) was expressed in *E. coli* as an N-terminal fusion to the GST-Tag according to standard protocols. The pull-down assay was performed in the Strep-Tactin buffer. The antibodies used for detecting the tags in the BTB/POZ-Strep was from Qiagen (catalog #34850) and those used for the tags in HA-Δ513 or the GST-VLRSgt were from Santa Cruz Biotechnology (catalog #: sc-7392 and sc-138).

Plant Transcription and Two-Hybrid Assays

*Arabidopsis thaliana* (Columbia) leaves were harvested from four-week-old plants grown at 21° C. (day) and 18° C. (night) with a ten-hour photoperiod and transferred to Petri dishes containing MS salts and micronutrients supplemented with B5 vitamins, 1% sucrose and 0.8% agar at a pH of 5.8. When required, filter-sterilized salicylic acid was added to the medium at a final concentration of 1 mM. Coating of the gold particles and general procedures and preparation of the biolistic experiments were as per the manufacturer's instructions (Bio-Rad). After bombardment, leaves were kept in the conditions described above for a period of 24 hours before assaying. Enzyme assays were performed using the Dual-Luciferase Reporter Assay® system (Promega) following the manufacturer's instructions. Luminescence was measured on a Berthold Lumat LB9507 Luminometer (Bad Wildbad, Germany) and the data obtained represented the value of the reporter gene divided by the value of the internal standard and expressed as Relative Luciferase Units. To increase signal-to-noise ratio in some experiments, qPCR was performed to measure the amount of Firefly and *Renilla* Luciferases mRNA. The data was reported as Relative Expression and represented the value of the reporter mRNA divided by the value of the internal standard mRNA. The ratio obtained for Gal4 DB was assigned an arbitrary value of 1. One μg of each effector plasmid, 1 μg of the firefly luciferase reporter plasmid, and 0.1 μg of the *renilla* internal standard plasmid were mixed together and the mixture was used to coat beads. This amount of DNA was used to perform 5 bombardments. Every bar in each graph represents five bombardments repeated five times on different days (n=25). The constructs used contained a Gal4 DB or VP16 N-terminal fusion or no fusion at all.

Equilibrium Dialysis and Scintillation Proximity Assays (SPA)

For equilibrium dialysis (as described in Freifelder, D. (1982). Physical Biochemistry: Applications to Biochemistry and Molecular Biology. W.H.Freeman and Company), two 500 μl chambers (A and B) were separated by a dialysis membrane with a cut-off of 3.5 kD. The buffer used in the system was the Strep-Tactin buffer. Radiolabeled SA (Perkin-Elmer, 50 mCi/mmol) was added in chamber A to a concentration of 10 μM SA, calculated based on the total volume of the system (A+B). Four μM of Δ513 protein or 0.8 μM of NPR1 protein were added to chamber B. The system was allowed to equilibrate at 4° C. for 24 hrs. Where indicated, EDTA was added to both chambers to a final concentration of 5 nM. After the 24-hr period, 100 μl from each chamber was removed and counted for $^{14}$Carbon, allowing for the calculation of SA concentration in each chamber. Given the dissociation reaction: Protein–$SA_{complex} \Leftrightarrow Protein_{free} + SA_{free}$; the dissociation constant $K_d$ equates: $[Protein_{free}] \times [SA_{free}]/[Protein-SA_{complex}]$. The different species were computed as follow: $[SA_{free}]=[SA_{chamber\ A}]$; $[Protein-SA_{complex}]=[SA_{chamber\ B}]-[SA_{chamber\ A}]$; $[Protein_{free}]=[Protein_{initial}]-[Protein-SA_{complex}]$.

For SPA (FIG. 7D-G), radiolabeled SA and NPR1 were incubated with 2 mg of Streptavidin SPA beads (PerkinElmer) in the Strep-Tactin buffer for 24 hrs at 4° C. on a rotation wheel. Specific binding was calculated by subtracting total cpm from non-specific cpm, which were counted by adding a 10-fold excess of cold SA.

For the saturation binding curves (FIGS. 1C and 7D/E), 0.8 μM of NPR1 protein was incubated with a final concentration of 0.007-14 μM [$^{14}$C]SA. The data was analyzed by non-linear regression using GraphPad PRISM 4 and fitted to a one-site-binding rectangular hyperbola. For homologous and heterologous competitive binding curves (FIGS. 1E/F and 7F/G), 0.08 μM of NPR1 protein was incubated with a final concentration of 0.07 μM [$^{14}$C]SA. Competitors were used at 0.1-100 times the concentration of hot ligand, except for BTH, INA, 5-CSA, 4-CSA, and 3,5-DCSA, which were used at 0.1-10 times the concentration of hot ligand, due to their low solubility in water.

Inductively Coupled Plasma-Mass Spectrometry (ICP-MS)

Optimized ICP-MS determinations were performed in a fashion previously described (Wang et al. (2011) J. Anal. At. Spectrom). Sulfur determinations were made using the Dynamic Reaction Cell ICP-MS with chemical resolution, facilitated by using oxygen to generate $SO^+$. ICP-MS intensities were converted to concentrations using calibration curves (Table S2). Protein concentrations were based on sulfur content. Proteins were hydrolysed in 68-70% nitric acid for 40 min and then diluted 40 times in metal-free water before analysis. The StrepTactin buffer run through the FPLC and through an empty (protein-free) StrepTactin column served as a baseline for metal contamination. ICP-MS intensities of the baseline were subtracted from those of the protein extracts.

Chromatography

Strep-tagged purified proteins in a final volume of 2 ml were subjected to gel filtration analysis on the Sephacryl S100 HR or Sephacryl S300 HR packed in 50 cm long HR 16 columns (GE Health) and equilibrated with S300 chromatography buffer (50 mM HEPES, pH 7.4, 250 mM NaCl. Elutions, in 0.5 ml fractions, were performed in the same buffer at a flow rate of 0.8 ml/min. Where indicated, proteins were incubated with 1 mM SA, 1 mM catechol, 1 mM 4-hydroxy benzoic acid, or 1 mM methyl-salicylate at room temperature for 30 min prior to chromatography as described above with the exception that the chromatography buffer was supplemented with 1 mM SA, 1 mM catechol, 1 mM 4-hydroxy benzoic acid, or 1 mM methyl-salicylate, respectively. In the case of the EDTA treatment, NPR1 was stripped of its metal by a 50 mM EDTA treatment of 30 min, followed by an incubation of 30 min with 1 mM SA prior to gel filtration. In this case, the chromatography buffer was supplemented with 1 mM SA.

Quantitative Reverse-Transcriptase Polymerase Chain Reaction

Total RNA was extracted from leaves using the Rneasy plant mini kit (Qiagen) according to the supplier's instructions. After treatment with Dnase I (Invitrogen), first strand cDNA synthesis was generated using SuperScript II reverse transcriptase (Invitrogen), and the $(dT)_{17}VN$ oligo in the presence of 0.4 U Rnasin (Fisher Scientific). The newly-synthesized cDNA was diluted 1/200 to reflect a concentration of 10 ng μL$^{-1}$ input total RNA. RT-PCR was performed on a CFX96 spectrofluorometric thermal cycler (BioRad). Firefly luciferase values were normalized against *Renilla*

Luciferase and PR-1 values against Ubiquitin5 (see Table 1 for primer sequence). All chemicals were used at a concentration of 300 µM, except for BTH, which was used at 100 µM due to its lower solubility in water. All treatments were for 12 hrs. Values consist of n=3 biological replicates and represent averages±1 SD.

Cross-Linked-Chromatin Chromatography (3C Method)

Plant treatment, cross-linking, sonication, and cross-linking reversal were performed as for chromatin-immunoprecipitation (Rochon et al., 2006). Chromatography was as described under "Chromatography". qPCR was performed with PR1 and Ubiquitin5 primers. PR-1 values were normalized against against Ubiquitin5 (see Table 1 for primer sequence).

TABLE 1

PCR Primers Used in this Study.

*Sequence in 5' to 3' Direction

Primers used for qRT-PCR

| | |
|---|---|
| PR1F | GCTCTTGTAGGTGCTCTTGTTCTTCC (SEQ ID NO: 1) |
| PR1R | AGTCTGCAGTTGCCTCTTAGTTGTTC (SEQ ID NO: 2) |
| UBQ5-1 | ACCTACGTTTACCAGAAAGAAGGAGTTGAA (SEQ ID NO: 3) |
| UBQ5-2 | AGCTTACAAAATTCCCAAATAGAAATGCAG (SEQ ID NO: 4) |

Primers used for 3C Method

| | |
|---|---|
| PR1a(-734) | GATCACCGATTGACATTGTA (SEQ ID NO: 5) |
| PR1b(-833) | GAACACAAAAGTAGATCGGT (SEQ ID NO: 6) |
| UBQ5a | GACGCTTCATCTCGTCC (SEQ ID NO: 7) |
| UBQ5b | GTAAACGTAGGTGAGTCCA (SEQ ID NO: 8) |

Primers used for Luciferase qRT-PCR

| | |
|---|---|
| FLucF | AGGTGGCTCCCGCTGAATTG (SEQ ID NO: 10) |
| FLucR | CATCGTCTTTCCGTGCTCCA (SEQ ID NO: 11) |
| RLucF | GTGGTAAACCTGACGTTGTA (SEQ ID NO: 12) |
| RlucR | CTTGGCACCTTCAACAATAG (SEQ ID NO: 13) |

*All PCR primers were synthesized by Integrated DNA Technologies, Inc.

Data Analysis

All graph results relating to Relative Luciferase Units and mRNA Relative Expression are reported as mean±1 standard deviation (SD) of 25 independent experiments. Comparisons were performed using two-tailed paired Student's t test. *$p<0.05$.

Results

NPR1 Binds Specifically to SA

To test whether NPR1 can bind SA directly, a classic method to assess $K_d$ values was used, which involved coupling NPR1 to a solid phase and incubating it with radiolabeled SA, followed by washes to remove unbound ligand and counting the amount of ligand bound to NPR1. This method did not yield a measurable apparent equilibrium dissociation constant ($K_d$) as the binding of SA to NPR1 was not above that observed with a solid phase containing no protein (FIG. 1A).

In light of the possibility that the washes alone might be sufficient to re-equilibrate SA between the solid and mobile phases, an equilibrium method that would avoid such a potential shortcoming was used. Using equilibrium dialysis (Freifelder, (1982), ibid; Piscitelli et al. (2010) Nature 468, 1129-1132), it was determined that NPR1 and radiolabeled SA could interact with each other, the amount of SA bound to NPR1 being close to 4-orders of magnitude above a no-protein experiment (FIG. 1B). From these data, a low apparent $K_d$ of 140±10 nM could be calculated (137±13 nM using the saturation curve in FIG. 1C). The data was best-fitted to a single-site-binding rectangular hyperbola (FIG. 1C), indicating that SA binds to one class of binding sites in NPR1. The maximum binding ($B_{max}$) was 0.96±0.01 mol SA per mol NPR1.

It was also tested which of the two domains (BTB/POZ or C-terminal transactivation domain (construct Δ513)) can directly interact with SA. The data demonstrated that the binding affinity of Δ513 ($K_d$ of 1.49±0.02 µM) for SA is more than 2-orders of magnitude above that of the BTB/POZ ($K_d$ of 597±14 µM) (FIG. 1B). The NPR1 $K_d$ is comparable to the $K_d$ found for other plant-hormone receptor-ligand interactions and is in accordance with the in vivo SA concentration of 0.36 µM (0.05 µg/g FW) reported in unstimulated *Arabidopsis* cells and 7.24 µM (1 µg/g FW) after challenge with an avirulent strain of *Pseudomonas syringae*.

Chemical specificity of SA-binding was also demonstrated with homologous and heterologous competitive binding curves (FIGS. 1E and F), which indicated that the structurally-related inactive analogs (FIG. 1G), i.e., catechol, methyl-salicylate, 4-hydroxy benzoic acid, and 3-hydroxy benzoic acid, do not interact with NPR1 with the same affinity as SA. In contrast, the structurally-related active analogs of SA (FIG. 1G), 4-chloro SA, 5-chloro SA and 3,5-dichloro SA, could bind NPR1 with a similar or slightly better affinity than SA, consistent with their capacity to trigger PR-1 expression in *Arabidopsis* (FIG. 1H). This excellent affinity, saturability, and chemical specificity of NPR1 for SA support a model in which NPR1 is an SA-receptor.

Figure 7:
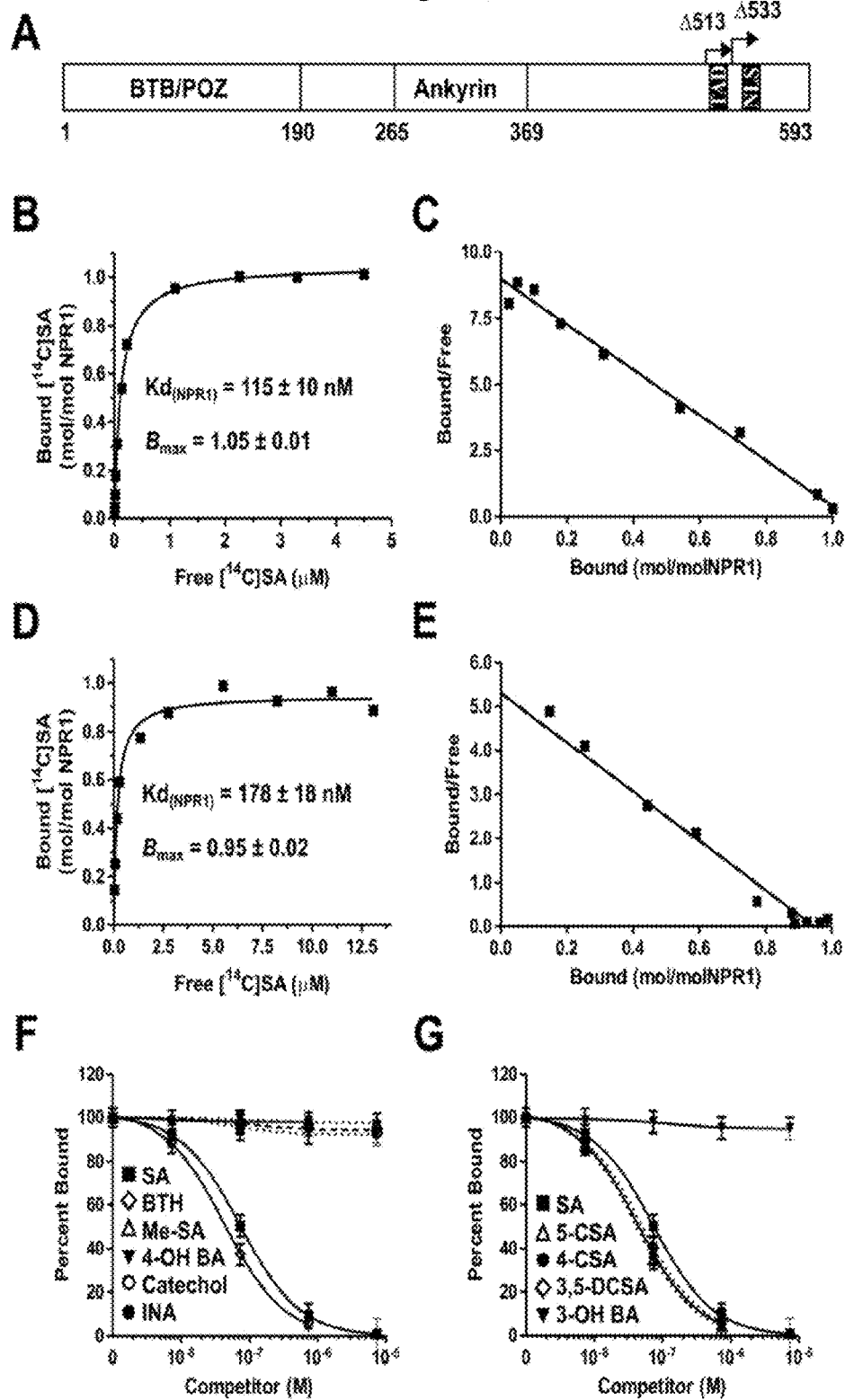
FIG. 7. Schematic of the NPR1 structure (A); Saturation binding of [$^{14}$C]SA to untagged NPR1 using equilibrium dialysis (B); Scatchard Plot (C) of the data in (B); Saturation binding of [$^{14}$C]SA to NPR1 using Scintillation Proximity Assay (D); Scatchard Plot (E) of the data in (D); Homologous and heterologous competitive binding curves for the [$^{14}$C]SA-NPR1 interaction using Scintillation Proximity Assay (F/G).

From these data, one can deduce that an electronegative functional groups, such as a hydroxyl group, in ortho position to another electronegative functional group, such as a free carboxylate, on the aromatic ring are two structural elements required for binding to NPR1. With this in mind, one can predict that the synthetic SAR and PR-1 expression inducer benzo(1,2,3)thiadiazole-7-carbothioic acid S-methyl ester (BTH) would bind NPR1, since it contains two sulfur atoms in positions geometrically equivalent to the oxygens in the carboxylate and hydroxyl group of SA (arrows on BTH; FIG. 1G). Indeed, BTH does bind NPR1 with a similar or slightly better affinity than SA (FIG. 1E), consistent with its capacity to induce PR-1 expression in *Arabidopsis* (FIG. 1H). However, a look at 2,6-dichloroisonicotinic acid (INA) reveals that it is similar to 3,5-dichloro SA, but that it is lacking the hydroxyl group (arrow on INA; FIG. 1G). Therefore, INA would not be predicted to bind NPR1 and indeed it did not (FIG. 1E). qRT-PCR reveals that INA was a poor inducer of PR-1 expression in *Arabidopsis* (FIG. 1H), 42 times less effective than an identical concentration of SA and 10 times less effective than an identical concentration of the weakest active SA analog, 4-chloro SA (FIG. 1I). These data suggest that INA may activate PR-1 through a mechanism different from that of SA. The binding data in FIG. 1 have been validated by a second approach, scintillation proximity assay (FIG. 7).

NPR1 Binds SA Through $Cys^{521/529}$ Via the Transition Metal Copper

Figure 2:
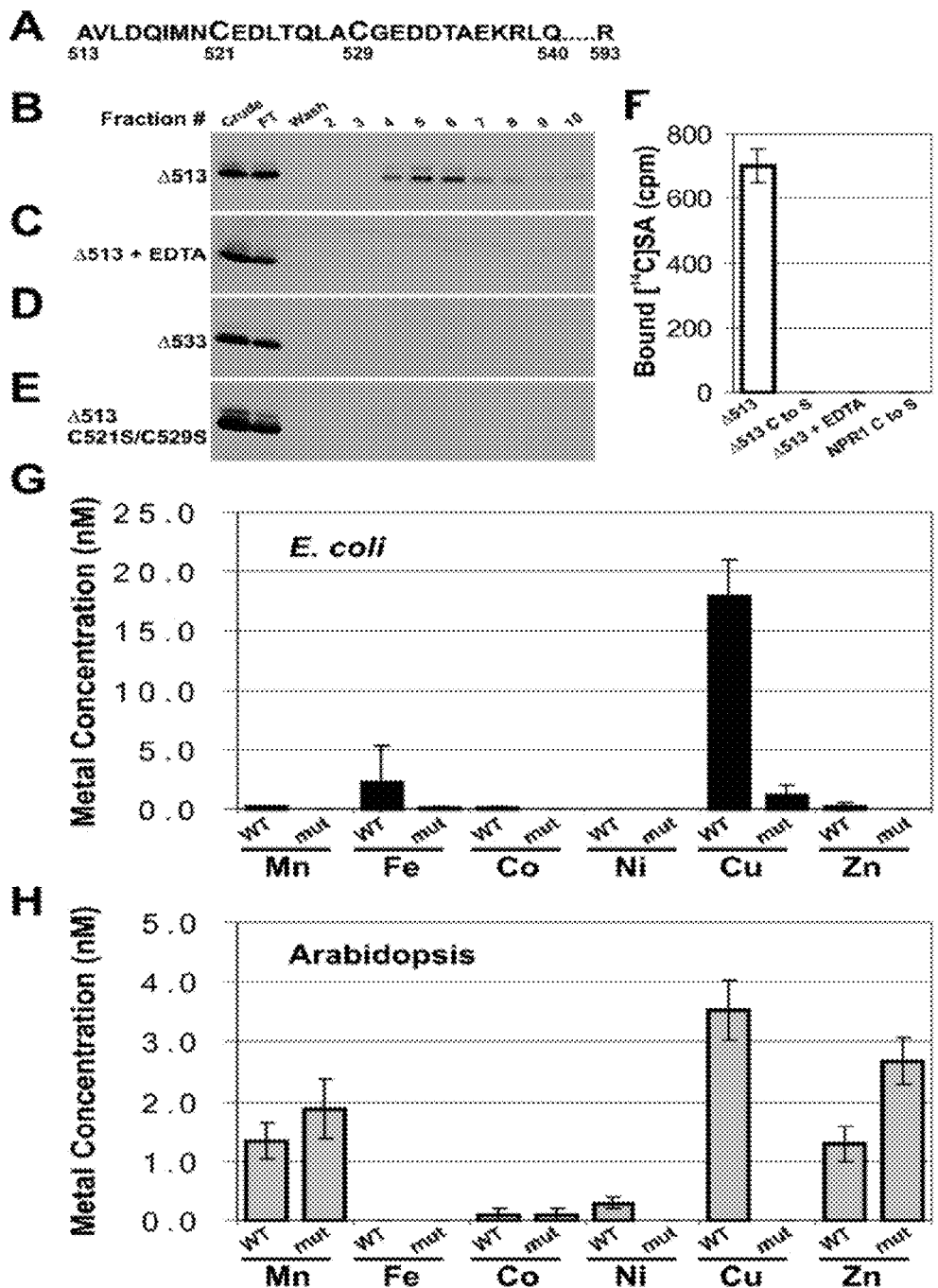
FIG. 2. (A) Sequence of the NPR1 transactivation domain (Δ513) showing $Cys^{521}$ and $Cys^{529}$ (note that NPR1 ends at amino acid 593); (B-E) immunoblots of HA-tagged NPR1 transactivation domains separated by immobilized metal-affinity chromatography (Ni-NTA) in the presence of either buffer alone, or buffer supplemented with EDTA; (F) [$^{14}C$] SA-binding assays of the transactivation domain of NPR1 (Δ513) using equilibrium dialysis; and Concentrations of various candidate d-block metals associated with *E. coli*-produced (G) and *Arabidopsis*-produced (H) NPR1 protein (WT/mutant).

It has been demonstrated that $Cys^{521/529}$ of NPR1 are required, along with SA treatment, for the activation of PR-1 in vivo and for the transactivating function of Δ513 and the full-length NPR1. Since SA can coordinate transition metals through its oxygen atoms, it was determined whether or not Δ513 could interact with a transition metal and whether this interaction would be dependent on $Cys^{521/529}$. To do so, Δ513 fused to an HA-tag was passed through an immobilized metal-affinity column bound to $Ni^{2+}$ (Ni-NTA) and eluted with imidazole. Despite the absence of a 6-histidine-tag on Δ513, the protein interacted with the metal-bound matrix and was eluted with imidazole just like a His-tagged protein would (FIG. 2B). Chelation of the $Ni^{2+}$ by EDTA concomitant with the extraction of the HA-tagged Δ513 abolished the recruitment to the NTA matrix (FIG. 2C), demonstrating that the binding of this protein is metal-dependent. The recruitment of this protein to the Ni-NTA matrix was also abolished when $Cys^{521/529}$ were both mutated to non-metal binding amino acids, e.g. serine residues (Δ513 C521S/C529S) or if the protein was further deleted by 20 amino acids (Δ533), suggesting that $Cys^{521/529}$ are critical to the transition-metal-binding activity of NPR1 (FIGS. 2D and E).

To further confirm that SA is perceived through cysteines in a metal-dependent manner, the capacity of both full-length NPR1 and Δ513 harboring C-to-S mutations at $Cys^{521/529}$ to interact with SA, using equilibrium dialysis was tested. In addition, the binding of SA to wild-type Δ513 was also evaluated in the presence of EDTA (FIG. 2F). Both metal chelation and the $Cys^{521/529}$ mutations drastically reduced the SA binding to the C-terminus of NPR1 by several orders of magnitude (FIG. 2F). Using these data, an apparent $K_d$ of 1.23±0.3 mM for Δ513 C to S, and ≥125 mM for Δ513+EDTA, could be calculated. These results support a model in which SA binds to NPR1 via $Cys^{521/529}$ through the coordination of SA by a transition metal.

It was then determined which of the transition metals (defined as d-block elements of the periodic table) that are most commonly found in living organisms might be associated with NPR1 in vivo. First, Δ513 fused to the Strep-tag was extracted from *E. coli* and purified on a StrepTactin column prior to metal analysis by Inductively Coupled Plasma-Mass Spectrometry (ICP-MS) as shown in Table 2.

TABLE 2

Slopes and coefficients of determination governing the ICP-MS calibration curves of the various elements studied in FIG. 2g and 2h.

| Element | Experiment 1 FIG. 2g | | Experiment 2 FIG. 2g | | Experiment 1 FIG. 2h | | Experiment 2 FIG. 2h | |
|---|---|---|---|---|---|---|---|---|
| | Slope (cps/nM)[4] | $R^2$ value | Slope (cps/nM) | $R^2$ value | Slope (cps/nM) | $R^2$ value | Slope (cps/nM) | $R^2$ value |
| $Mn^1$ | 1879.7 | 0.99998 | 1604.1 | 0.99997 | 1600.5 | 0.99994 | 1559.6 | 0.99991 |
| $Fe^2$ | 490.42 | 0.99998 | 122.92 | 1 | 121.6 | 0.99981 | 98.839 | 0.99963 |
| $Co^1$ | 1845.7 | 0.99999 | 1553.9 | 1 | 1667 | 0.99961 | 1548.9 | 0.99976 |
| $Ni^1$ | 414.63 | 0.99869 | 347.19 | 0.99888 | 371.83 | 0.99984 | 342.18 | 0.99978 |
| $^{63}Cu^1$ | 1018.3 | 0.99999 | 834.14 | 0.99997 | 909.93 | 0.99974 | 832.01 | 0.99966 |
| $Zn^1$ | 276.75 | 0.99999 | 236.35 | 0.99996 | 263.59 | 0.99982 | 238.98 | 0.99993 |
| $S^3$ | 26.668 | 0.99993 | 26.944 | 0.99996 | 1600.5 | 0.99994 | 1559.6 | 0.99991 |

[1]Elements were detected under standard mode.
[2]Fe was detected under DRC mode with $NH_3$.
[3]Sulfur was used to determine the protein concentration of wild-type Δ513 and Δ513 bearing cysteine-to-serine mutations at positions 521 and 529. Sulfur was detected under DRC mode with $O_2$.
[4]cps (counts per second). The equation was calculated by Linear Thru Zero.

The data indicated that the C-terminus of NPR1 associated preferentially with the transition metal, copper (FIG. 2G), and that the mutations of $Cys^{521/529}$ severely curtailed the capacity of Δ513 to interact with copper. Second, full-length wild-type NPR1 was immunoprecipitated from *Arabidopsis* before metal analysis by ICP-MS. As a negative control, plants expressing a variant of full-length NPR1 lacking $Cys^{521/529}$ was used. The results (FIG. 2H) were consistent with the observations made from *E. coli*-produced proteins in that NPR1 associated preferentially with copper and to a lesser extent with nickel. Mutations of $Cys^{521/529}$ severely curtailed the capacity of NPR1 to interact with these metals. Contamination by manganese and zinc was present in *Arabidopsis* extracts. However, detection of Mn and Zn did not depend on $Cys^{521/529}$.

The Conformation of NPR1 and Δ513 is Altered by SA

Figure 3:
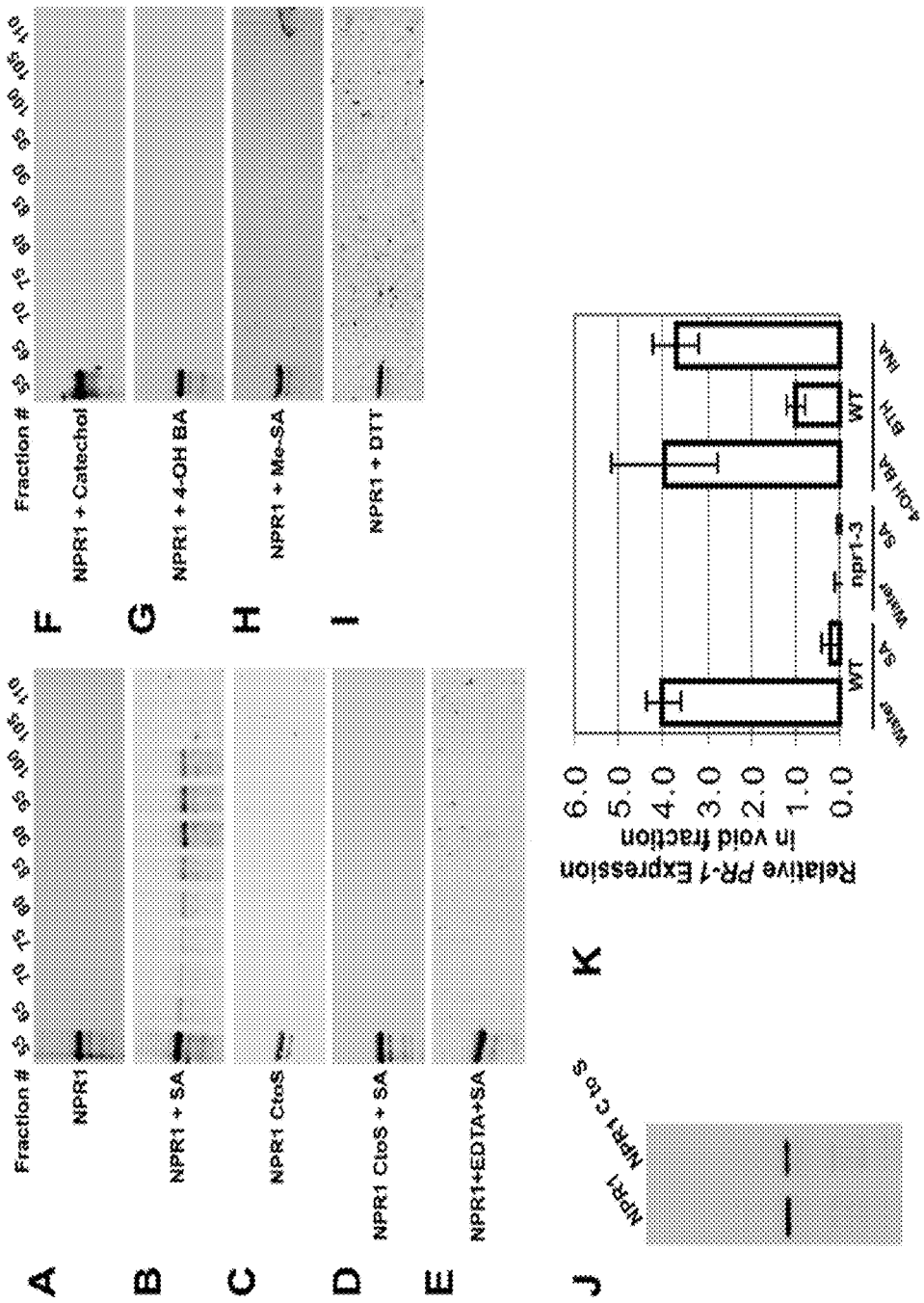
FIG. 3. Immunoblot analysis of protein fractions from an S300 elution profile of (A) untreated, (B) SA-treated, (E) EDTA and SA-treated, (F) Catechol-treated, (G) 4-hydroxybenzoic acid-treated, (H) methyl-salicylate-treated or (I) DTT-treated Strep-tagged NPR1, using an anti-Strep antibody; Immunoblot analysis, of protein fractions from an S300 elution profile of (C) untreated or (D) SA-treated Strep-tagged NPR1 harboring a Cys-to-Ser substitution; Coomassie stain of an SDS-PAGE gel showing purified NPR1 and the NPR1 mutant bearing a cysteine-to-serine substitution at positions 521 and 529 (J); and 3C Method showing the presence/absence of NPR1-dependent oligomer on the PR-1 promoter(K).

To explore the effect of SA on the conformation of NPR1, gel filtration experiments were performed (FIG. 3). In the absence of SA, NPR1 eluted in the void volume of a Sephacryl S300 column (FIG. 3A). However, upon treatment with SA, NPR1 redistributed to the included volume (FIG. 3B) with a stoichiometry consistent with that of a dimer (Tables 3 and 4).

TABLE 3

Predicted and Observed Elution Volumes Establishing the Stoichiometry of NPR1 in 1 mM SA on the S300 column.

| Anticipated Species | MW (kDa) | LogMW | Kav (Predicted) | Predicted Ve (mL) | Predicted Fraction number |
|---|---|---|---|---|---|
| NPR1 monomer | 66 | 1.819543936 | 0.377677209 | 61.60482554 | 103-4 |
| NPR1 dimer | 132 | 2.120573931 | 0.3003125 | 56.76953123 | 94 |
| NPR1 trimer | 198 | 2.29666519 | 0.255057046 | 53.94106538 | 88 |
| NPR1 tetramer | 264 | 2.421603927 | 0.222947791 | 51.93423692 | 84 |

Comments: In FIG. 3b (NPR1 + SA panel), the highest amount of NPR1 found in the included volume was in fractions 90 and 95. Since the predicted fraction number for the NPR1 dimer is 94 (a number between 90 and 95), it would suggest that NPR1 exists as a dimer after SA treatment.

TABLE 4

Elution Fractions and Corresponding Volumes for Gel filtration Analyses.

| | Elution volume (ml) | |
|---|---|---|
| Fraction # | From | To |
| 50 | 34.567 | 35.067 |
| 55 | 37.117 | 37.617 |
| 60 | 39.601 | 40.101 |
| 65 | 42.118 | 42.618 |
| 70 | 44.635 | 45.135 |
| 75 | 47.119 | 47.619 |
| 80 | 49.636 | 50.136 |
| 85 | 52.16 | 52.66 |
| 90 | 54.644 | 55.144 |
| 95 | 57.127 | 57.627 |
| 100 | 59.618 | 60.118 |
| 105 | 62.135 | 62.635 |
| 110 | 64.659 | 65.159 |
| 115 | 67.143 | 67.643 |

Comments: Each fraction contains approximately 0.5 ml. Since the amount of NPR1 was too low to show observable peaks on the chromatogram, this table is provided to facilitate the conversion between fraction # and elution volume. The fraction # corresponds to the fraction # in FIG. 3.

Mutations of $Cys^{521/529}$ or chelation of the metal by EDTA abolished the NPR1 conformation change observed after treatment with SA (FIGS. 3C, D and E), confirming the requirement for $Cys^{521/529}$ and a metal for SA interaction (FIG. 2F). A chemical specificity test using catechol, 4-hydroxy benzoic acid, and methyl-salicylate indicated that these inactive structural analogs do not alter the conformation of NPR1 (FIGS. 3F, G and H), consistent with their reduced capacity to interact with NPR1 (FIG. 1E). Finally, treatment of NPR1 with the reducing agent DTT did not induce a redistribution of the protein to the included volume (FIG. 3I), indicating that reducing conditions are not required or sufficient for the SA-induced NPR1-redistribution observed here. A typical Coomassie stained gel of the void fraction reveals that NPR1 and NPR1 C521S/C529S were the major protein component of the void (FIG. 3J) and that therefore the oligomers are unlikely to be due to the presence of contaminating E. coli proteins.

Although there are no decisive methods to test the stoichiometry of a protein in vivo, it was determined whether or not NPR1-dependent oligomers form on DNA in vivo by combining chromatin cross-linking, gel filtration, and qPCR (the 3C Method). The rationale was that, if an NPR1-dependent oligomer forms on the PR1 promoter in vivo, the presence of PR1 should be detectable by qPCR in the void fraction of an S300 after the chromatin had been cross-linked and sheared by sonication. FIG. 3K indicates that in wild-type plants (WT), such an oligomer forms on the PR-1 promoter (region −734 to −833 of the promoter) in the absence of SA (water), but not after a treatment with SA. Repeating the experiment in the npr1-3 mutant background demonstrated that this oligomer depended on the presence of NPR1. Treatment of wild-type Arabidopsis with the inactive SA analog, 4-hydroxy benzoic acid (4-OH BA), did not reduce the amount of NPR1-dependent oligomer. These in vivo data are consistent with the in vitro data of FIGS. 3A, B and G. Although BTH treatment could not be used in the in vitro chromatography due to its low solubility in water, it is assumed that BTH would also disassemble an NPR1 oligomer since it is an active functional analog of SA and it can directly bind NPR1 (FIGS. 1E and H). Performing the 3C method on plants treated with BTH revealed that, like SA, this active analog also reduced the amount of NPR1-dependent oligomer on the PR-1 promoter (FIG. 3K). By contrast, INA, which did not interact with NPR1 in vitro and did not activate PR-1 to the same extent as SA or BTH (FIGS. 1E and H), did not affect the NPR1-dependent oligomer on the PR-1 promoter (FIG. 3K). This result further suggests that INA may not be a functional analog of SA.

Figure 4:
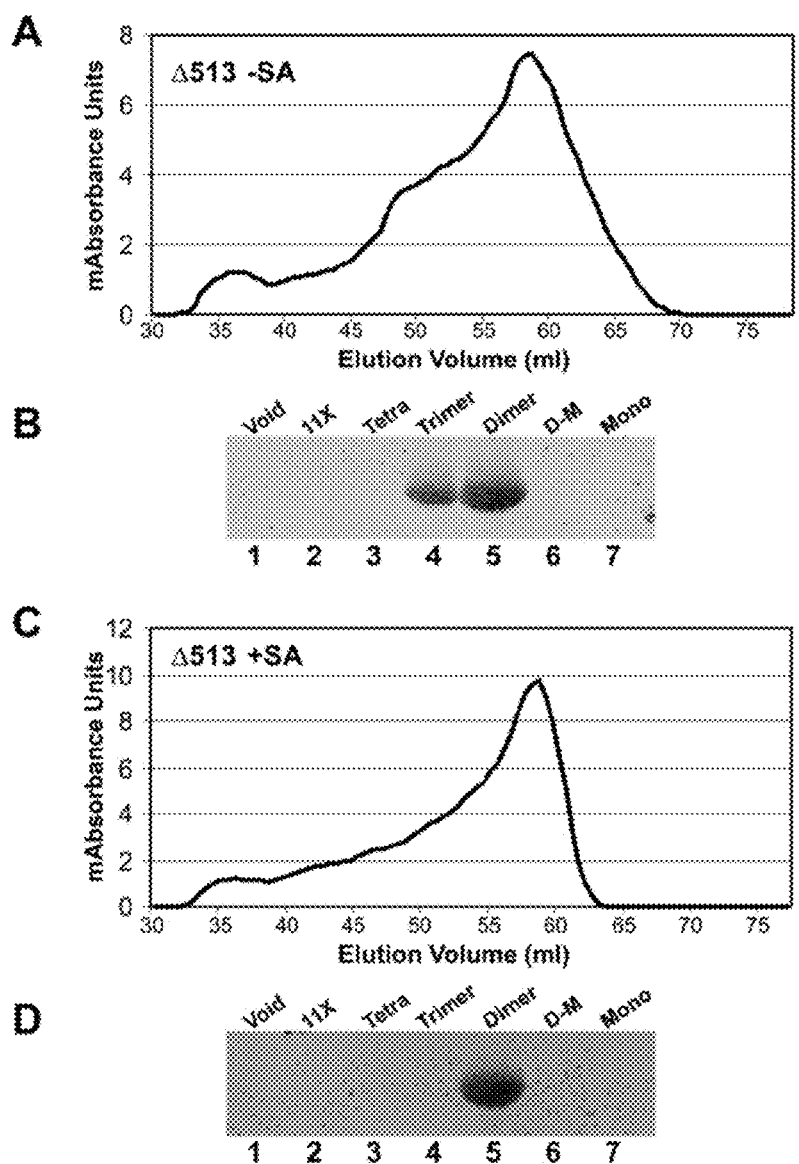
FIG. 4. S100 gel filtration chromatogram illustrating the elution profile of purified Strep-tagged Δ513 (A) untreated or (C) treated with 1 mM SA; and Immunoblot, using an anti-Strep antibody, of fractions (B and D) corresponding to theoretical peaks and taken from the chromatograms in (A) and (C).

The conformation of Δ513 was also investigated by gel filtration. Before and after SA-treatment, Δ513 was found in the included volume of a Sephacryl S100 column (FIG. 4). The stoichiometry of the untreated Δ513 was consistent with that of both a dimer and a trimer (FIGS. 4A and B), while the stoichiometry of the SA-dependent redistributed form of Δ513 was consistent with that of a dimer (FIGS. 4C/D and Table 5).

TABLE 5

Predicted and Observed Elution Volumes Establishing the Stoichiometry of Δ513 in 1 mM SA on the S100 column.

| Anticipated Species | MW (kDa) | LogMW | Kav (Predicted) | Predicted Ve (mL) | Observed Ve (mL) −SA | Observed Ve (mL) +SA |
|---|---|---|---|---|---|---|
| Δ513 monomer | 10.79 | 1.033021 | 0.489456 | 66.17234571 | — | — |
| Δ513 dimer | 21.58 | 1.334051 | 0.348664 | 57.25741343 | 58.78 | 57.18 |
| Δ513 trimer | 32.37 | 1.510143 | 0.266306 | 52.04251235 | 52.51 | — |
| Δ513 tetramer | 43.16 | 1.635081 | 0.207872 | 48.34248115 | — | — |
| Δ513 11× | 118.69 | 2.074414 | 0.002397 | 35.33174711 | 35.79 | 35.79 |

However, the elution volumes of the dimer in the untreated (58.78 mL) versus the SA-treated (57.18 mL) Δ513 were different and therefore indicated that these dimer may not have the same conformation. The elution volume of the SA-dependent dimer was closer to that of the theoretical dimer (57.26 mL).

SA Disrupts the BTB/POZ-Transactivation Domain Interaction

Figure 5:
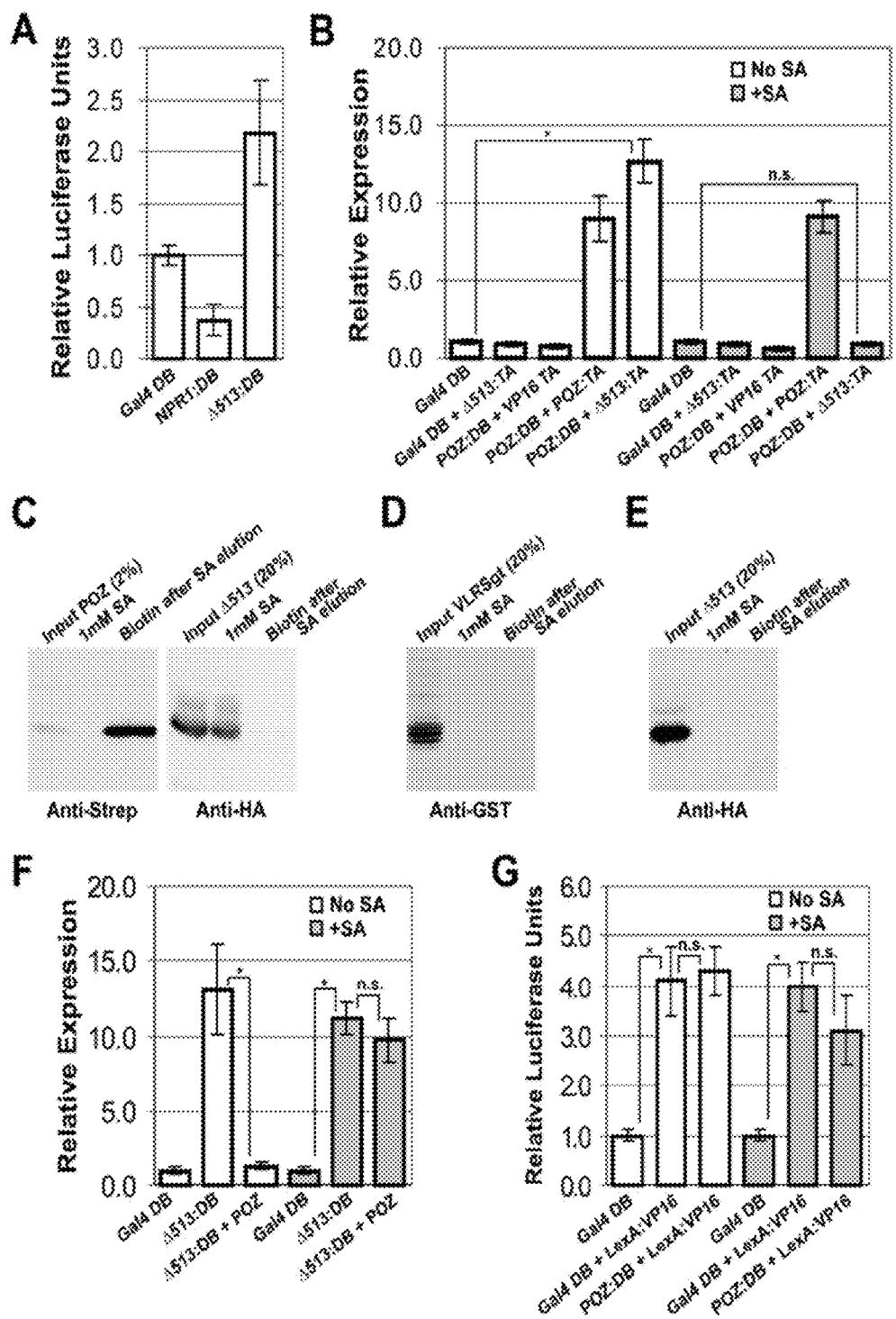
FIG. 5. (A) In vivo transcription assays showing that the NPR1 C-terminal transactivation domain (Δ513:DB) can activate the transcription of a reporter gene in the absence of SA-treatment; (B) In vivo plant two-hybrid assays showing that Δ513:DB can only interact with the NPR1 BTB/POZ domain (POZ:DB) in the absence of SA; (C) Pull-down assay using the BTB/POZ fused to the Strep-Tag and coupled to the StrepTactin solid-phase and the Δ513 fused to the HA-Tag; (D) Pull-down assay using the BTB/POZ fused to the Strep-Tag and coupled to the StrepTactin solid-phase and the VLRSgt protein (a glucosyltransferase unrelated in sequence to Δ513) fused to the GST-tag; (E) Pull-down assay using the empty StrepTactin solid-phase and the Δ513 fused to the HA-Tag; (F) In vivo transcription assays testing the transactivation properties of Δ513:DB, both alone and in complex with the NPR1 BTB/POZ (POZ) not fused to any domain; (G) In vivo transcription assays assessing the potential transcriptional repression conferred by the NPR1 BTB/POZ domain (POZ) tethered to DNA through the Gal4 DNA-binding domain (:DB).

When tethered to the Gal4 DNA-binding domain (DB) in an in vivo plant transcription assay, the transactivation domain of NPR1 (construct Δ513) can activate transcription in the absence of SA-treatment, but tethering of the full-length NPR1 did not (FIG. 5A), suggesting the presence of an auto-inhibitory domain in NPR1. Since BTB/POZ domains can be autoinhibitory, it was determined whether or not the NPR1 BTB/POZ can interact with the NPR1 transactivation domain. A plant two-hybrid system in the native organism, Arabidopsis, was used where the BTB/POZ was fused to the DB (POZ:DB) and the Δ513 was fused to the VP16 transactivation domain (Δ513:TA) (FIG. 5B). Here the reporter gene was monitored through its mRNA as opposed to its enzyme activity, which provided a greater signal-to-noise ratio (see Experimental Procedures). BTB/POZ self-association (POZ:DB+POZ:TA) in the absence or presence of SA served as a positive control. The interaction between the NPR1 BTB/POZ and its transactivation domain (POZ:DB+Δ513:TA) was observable in the absence of SA (significantly different from Gal4 DB, $p<0.05$), but not after SA-treatment (not significantly different from Gal4 DB, $p>0.05$), indicating that SA disrupts the BTB/POZ-Δ513 association (FIG. 5B).

Given that the plant two-hybrid system is an in vivo method of analysis, an indirect effect of SA on the interaction of the BTB/POZ and the C-terminus of NPR1 cannot be ruled out. Thus, the interaction in vitro in a pull-down assay (FIG. 8) was tested. Because the BTB/POZ was eluted from the solid support with the competing ligand, desthiobiotin, but not with 1 mM SA (FIG. 5C, left panel), it was concluded that SA, at the concentration tested, did not disrupt the Strep-tag/StrepTactin interaction. The pull-down indicated that the BTB/POZ interacted with Δ513, but that the interaction was disrupted by 1 mM SA (FIG. 5C, right panel). No Δ513 could be further eluted by desthiobiotin, indicating that SA displaced all of the Δ513 from the solid phase (FIG. 5C, right panel). As negative controls, first an unrelated protein (VLRSgt) was shown not to interact with BTB/POZ (FIG. 5D) and secondly Δ513 was shown not to interact with the solid support in the absence of BTB/POZ (FIG. 5E). Together these data demonstrate that SA directly disrupts the BTB/POZ-Δ513 interaction, which is consistent with the conformation change of NPR1 and Δ513 brought about by SA (FIGS. 3A and B, FIG. 4).

The NPR1 BTB/POZ Inhibits the Transactivation Potential of Δ513

It was then determined whether or not the BTB/POZ could modulate the transcriptional properties of Δ513 (FIG. 5F). When Δ513:DB was co-expressed in Arabidopsis leaves with the BTB/POZ (not fused to any foreign transcription activation or DNA-binding domain), expression of the reporter gene in untreated cells was reduced to background levels. However, the transcription activity of Δ513 in SA-treated cells was unaffected by the BTB/POZ, consistent with the fact that these two proteins could only interact in the absence of SA (FIG. 5B). In an in vivo plant repression assay, where the reporter gene is first activated by LexA:VP16 before testing for repression using a Gal 4:DB fusion, the NPR1 BTB/POZ did not appear to repress the promoter back to basal (Gal4 DB) level (FIG. 5G). These data revealed the autoinhibitory capacity of the BTB/POZ despite it not being an autonomous transcriptional repression domain. Therefore, in the absence of SA, the BTB/POZ must have masked the interface on the C-terminal transactivation domain required for its function.

Discussion

Given the saturability by SA, the low $K_d$, and the chemical specificity of the SA-NPR1 interaction, which are hallmarks of a receptor, NPR1 is undeniably an SA-receptor.

Figure 6:
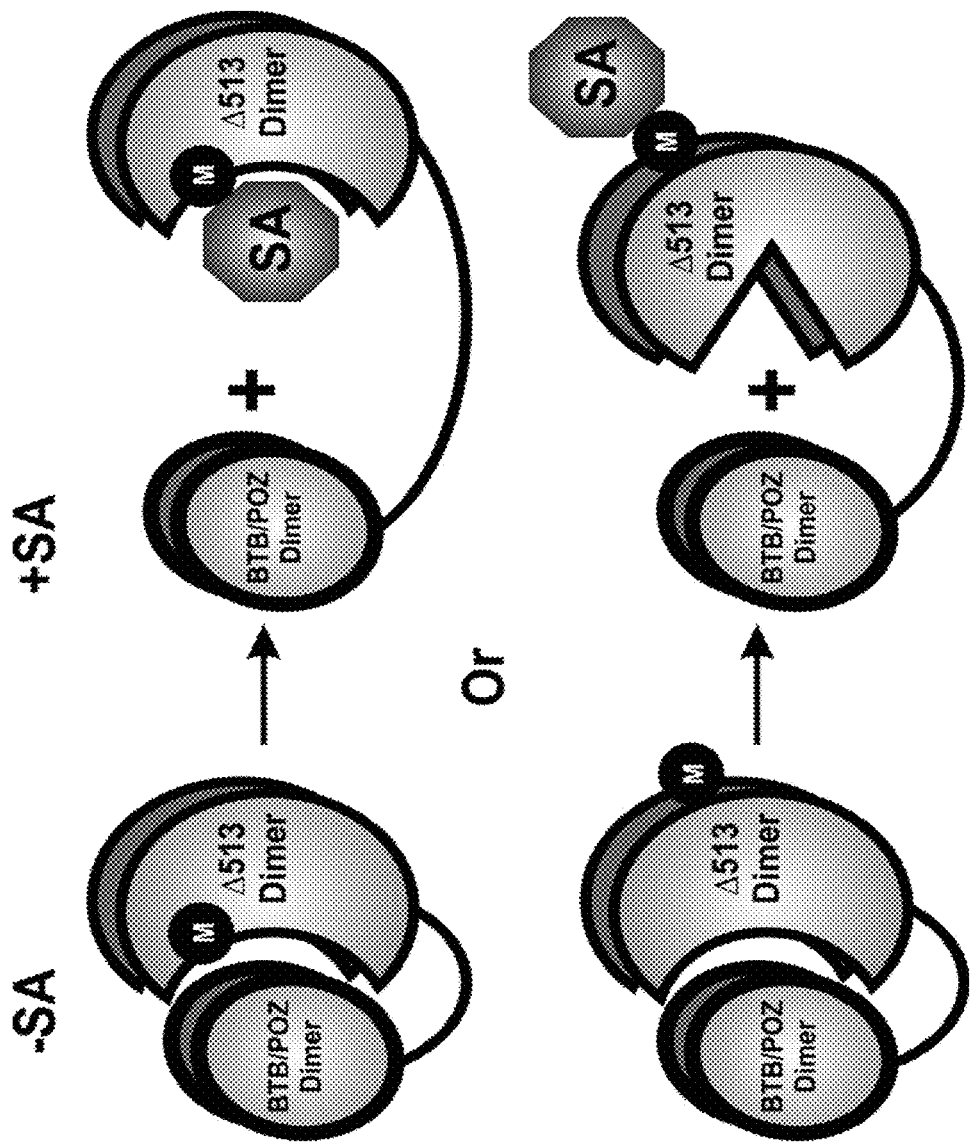
FIG. 6. Schematic illustrating the interaction between NPR1's C-Terminal Transactivation Domain (Δ513) and N-Terminal Auto-Inhibitory Domain (BTB/POZ).

Direct binding of SA by the receptor, NPR1, reorganizes the conformation of an NPR1-dependent oligomer at the PR-1 promoter and abolishes the interaction between the auto-inhibitory N-terminal BTB/POZ domain and the C-terminal transactivation domain of NPR1 (FIG. 6). Thus, a clear mechanistic path is established between the sensing of SA by NPR1 and the unveiling of the NPR1 transcriptional activation domain, a prerequisite to PR-1 gene activation.

The invention claimed is:

1. A method of identifying a small molecule candidate compound that enhances plant immunity comprising the step of screening a candidate small molecule compound for binding to a C-terminal transactivation domain of an NPR1 protein, and determining whether or not the small molecule binds to the C-terminal transactivation domain, wherein a compound that exhibits a binding affinity for the C-terminal transactivation domain is a candidate compound that may enhance plant immunity.

2. The method of claim 1, additionally comprising the step of determining whether or not binding of the small molecule to the C-terminal transactivation domain is metal dependent, wherein metal dependent binding indicates that the compound is a candidate compound that may enhance plant immunity.

3. The method of claim 2, wherein a determination of metal-dependent binding of the small molecule to the C-terminal transactivation domain is conducted in the absence of a metal.

4. The method of claim 2, wherein a determination of metal-dependent binding is conducted in the presence of a metal chelator.

5. The method of claim 2, wherein a determination of metal-dependent binding is conducted in the presence of a C-terminal transactivation domain in which $Cys^{521/529}$ of the transactivation domain are mutated to non-metal binding amino acids.

6. The method of claim 2, wherein the determination of metal-dependent binding is conducted in the presence of a truncated C-terminal transactivation domain in which a region including $Cys^{521/529}$ of the transactivation domain is removed.

7. The method of claim 1, wherein the compound exhibits a binding affinity for the C-terminal transactivation domain of about 50 µM or less.

8. The method of claim 2, wherein the compound exhibits a binding affinity for the C-terminal transactivation domain of about 10 µM or less.

9. The method of claim 1, wherein the compound has the general formula:

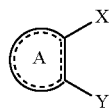

wherein X and Y are each an electronegative functional group that together can coordinate a transition metal; and ring A is a hydrophobic cyclic core.

* * * * *

SEQUENCE LISTING

```
<160> NUMBER OF SEQ ID NOS: 17

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gctcttgtag gtgctcttgt tcttcc                                          26

<210> SEQ ID NO 2
<211> LENGTH: 26
<212> TYPE: DNA
<213> ORGANISM: Artificial Sequence
<220> FEATURE:
<223> OTHER INFORMATION: primer

<400> SEQUENCE: 2
agtctgcagt tgcctcttag ttgttc                                          26
```

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
acctacgttt accagaaaga aggagttgaa                                    30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
agcttacaaa attcccaaat agaaatgcag                                    30

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gatcaccgat tgacattgta                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gaacacaaaa gtagatcggt                                               20

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
gacgcttcat ctcgtcc                                                  17

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
gtaaacgtag gtgagtcca                                                19

<210> SEQ ID NO 9
<211> LENGTH: 20
<212> TYPE: DNA
<213> ORGANISM: Artificial Sequence
<220> FEATURE:

<223> OTHER INFORMATION: primer

<400> SEQUENCE: 9
aggtggctcc cgctgaattg                                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
catcgtcttt ccgtgctcca                                                    20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gtggtaaacc tgacgttgta                                                    20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cttggcacct tcaacaatag                                                    20

<210> SEQ ID NO 13
<211> LENGTH: 81
<212> TYPE: PRT
<213> ORGANISM: Arabidopsis thaliana

<400> SEQUENCE: 13

Ala Val Leu Asp Gln Ile Met Asn Cys Glu Asp Leu Thr Gln Leu Ala
1               5                   10                  15

Cys Gly Glu Asp Asp Thr Ala Glu Lys Arg Leu Gln Lys Lys Gln Arg
            20                  25                  30

Tyr Met Glu Ile Gln Glu Thr Leu Lys Lys Ala Phe Ser Glu Asp Asn
        35                  40                  45

Leu Glu Leu Gly Asn Ser Ser Leu Thr Asp Ser Thr Ser Ser Thr Ser
    50                  55                  60

Lys Ser Thr Gly Gly Lys Arg Ser Asn Arg Lys Leu Ser His Arg Arg
65                  70                  75                  80

Arg

<210> SEQ ID NO 14
<211> LENGTH: 81
<212> TYPE: PRT
<213> ORGANISM: Theobroma cacao

<400> SEQUENCE: 14

Glu Val Leu Asn Lys Ile Met Asp Ala Asp Asp Leu Ser Gln Leu Ala
1               5                   10                  15

Cys Gly Gly Asn Asp Thr Pro Glu Glu Arg Leu Val Lys Lys Gln Arg

```
                    20                  25                  30

Tyr Val Glu Leu Gln Asp Val Leu Ser Lys Ala Phe Asn Glu Asp Lys
            35                  40                  45

Val Glu Phe Asp Arg Ser Thr Ile Ser Ser Ser Ser Ser Lys Ser
    50                  55                  60

Ile Gly Val Ser Arg Pro Asn Gly Lys Leu Thr Gly Ser Gly Arg Gly
65                  70                  75                  80

Gly

<210> SEQ ID NO 15
<211> LENGTH: 78
<212> TYPE: PRT
<213> ORGANISM: Gossypium hirstum

<400> SEQUENCE: 15

Glu Val Leu Asn Lys Ile Met Asp Ala Asp Leu Ser Gln Leu Ala
1               5                   10                  15

Cys Gly Gly Ile Asp Thr Ala Glu Glu Arg Val Val Lys Arg Gln Arg
            20                  25                  30

Tyr Met Glu Leu Gln Asp Val Leu Ser Lys Ala Phe His Glu Asp Lys
            35                  40                  45

Glu Gln Phe Asp Arg Ser Ala Ile Ser Ser Ser Ser Ser Lys Ser
    50                  55                  60

Ile Val Val Thr Gly Pro Lys Gly Lys Ala His Cys Tyr Ser
65                  70                  75

<210> SEQ ID NO 16
<211> LENGTH: 78
<212> TYPE: PRT
<213> ORGANISM: Nicotiana tabacum

<400> SEQUENCE: 16

Glu Val Leu Asn Lys Ile Met Asp Ala Asp Asp Leu Ser Glu Ile Ala
1               5                   10                  15

Tyr Met Gly Asn Asp Thr Ala Glu Glu Arg Gln Leu Lys Lys Gln Arg
            20                  25                  30

Tyr Met Glu Leu Gln Glu Ile Leu Thr Lys Ala Phe Thr Glu Asp Lys
            35                  40                  45

Glu Glu Phe Asp Lys Thr Asn Asn Ile Ser Ser Cys Ser Ser Thr
    50                  55                  60

Ser Lys Gly Val Asp Lys Pro Asn Lys Leu Pro Phe Arg Lys
65                  70                  75

<210> SEQ ID NO 17
<211> LENGTH: 67
<212> TYPE: PRT
<213> ORGANISM: Oryza sativa

<400> SEQUENCE: 17

Asn Val Leu Asp Lys Ile Met Asp Glu Thr Asp Pro Val Ser Leu
1               5                   10                  15

Gly Arg Asp Thr Ser Ala Glu Lys Arg Lys Arg Phe His Asp Leu Gln
            20                  25                  30

Asp Val Leu Gln Lys Ala Phe His Glu Asp Lys Glu Asn Asp Arg
            35                  40                  45
```

```
Ser Gly Leu Ser Ser Ser Ser Ser Thr Ser Ile Gly Ala Ile Arg
    50                  55                  60

Pro Arg Arg
65
```